United States Patent
Steffensmeier et al.

(10) Patent No.: US 7,282,054 B2
(45) Date of Patent: Oct. 16, 2007

(54) ADJUSTABLE CUT BLOCK

(75) Inventors: Scott J. Steffensmeier, Warsaw, IN (US); Adam H. Sanford, Warsaw, IN (US)

(73) Assignee: Zimmer Technology, Inc., Chicago, IL (US)

( * ) Notice: Subject to any disclaimer, the term of this patent is extended or adjusted under 35 U.S.C. 154(b) by 441 days.

(21) Appl. No.: 10/746,384

(22) Filed: Dec. 26, 2003

(65) Prior Publication Data
US 2005/0149037 A1 Jul. 7, 2005

(51) Int. Cl.
*A61B 17/58* (2006.01)
(52) U.S. Cl. ............... 606/96; 606/86; 606/87; 606/88; 623/20.32
(58) Field of Classification Search .......... 606/79, 606/86, 87, 88, 96
See application file for complete search history.

(56) References Cited

U.S. PATENT DOCUMENTS

| 4,566,448 | A | * | 1/1986 | Rohr, Jr. ............ 606/88 |
| 5,540,695 | A | * | 7/1996 | Levy ............ 606/87 |
| 5,597,379 | A | * | 1/1997 | Haines et al. ............ 606/80 |
| 5,601,563 | A | * | 2/1997 | Burke et al. ............ 606/86 |
| 5,688,280 | A | * | 11/1997 | Booth et al. ............ 606/88 |
| 5,860,980 | A | * | 1/1999 | Axelson et al. ............ 606/88 |
| 5,925,049 | A | * | 7/1999 | Gustilo et al. ............ 606/82 |
| 6,478,799 | B1 | * | 11/2002 | Williamson ............ 606/90 |

OTHER PUBLICATIONS

Zimmer, Extramedullary Surgical Approach for the M/G™ Unicompartmental Knee Minimally Invasive Surgical Technique, 2001.

* cited by examiner

*Primary Examiner*—Eduardo C. Robert
*Assistant Examiner*—James L. Swiger
(74) *Attorney, Agent, or Firm*—Baker & Daniels LLP

(57) ABSTRACT

The present invention provides a cut block for cutting the femur and tibia during knee replacement surgery.

10 Claims, 6 Drawing Sheets

ADJUSTABLE CUT BLOCK

BACKGROUND

The invention relates to cut blocks for guiding a cutter to cut a bone to receive a knee prosthesis. More particularly, the invention relates to adjustable cut blocks.

Degenerative and traumatic damage to the articular cartilage of the knee joint can result in pain and restricted motion. Prosthetic joint replacement is frequently utilized to alleviate the pain and restore joint function. In this procedure, the damaged compartments of the joint are cut away and replaced with prosthetic components. Typically a cut guide is used to guide a cutter such as a saw blade or bur to cut a desired portion of the bone.

SUMMARY

The present invention provides a cut block for cutting the femur and tibia during knee replacement surgery.

In one aspect of the invention, a cut block for cutting the femur and tibia during knee replacement surgery includes a body having a plurality of cutter guides for guiding a cutter to cut the femur and tibia. The body has a posterior face and first and second posteriorly projecting reference surfaces. The vertical spacing of the first and second reference surfaces is adjustable to space the tibia from the femur.

In another aspect of the invention, a method for cutting the femur and tibia during knee replacement surgery includes exposing a portion of the knee joint; providing a cut block including a body having cutter guides for guiding a cutter to cut the femur and tibia, the body having a posterior face and first and second reference surfaces, the vertical spacing between the first and second reference surfaces being adjustable; positioning the knee in a desired knee joint alignment; contacting one of the tibia and femur with one of the reference surfaces; contacting the other of the tibia and femur with the other of the reference surfaces; adjusting the vertical spacing of the reference surfaces to hold the joint in the desired alignment; and guiding a cutter with the cutter guides of the cut block to cut the femur and tibia.

BRIEF DESCRIPTION OF THE DRAWINGS

Various embodiments of the present invention will be discussed with reference to the appended drawings. These drawings depict only illustrative embodiments of the invention and are not to be considered limiting of its scope.

DESCRIPTION OF THE ILLUSTRATED EMBODIMENTS

Figure 1:
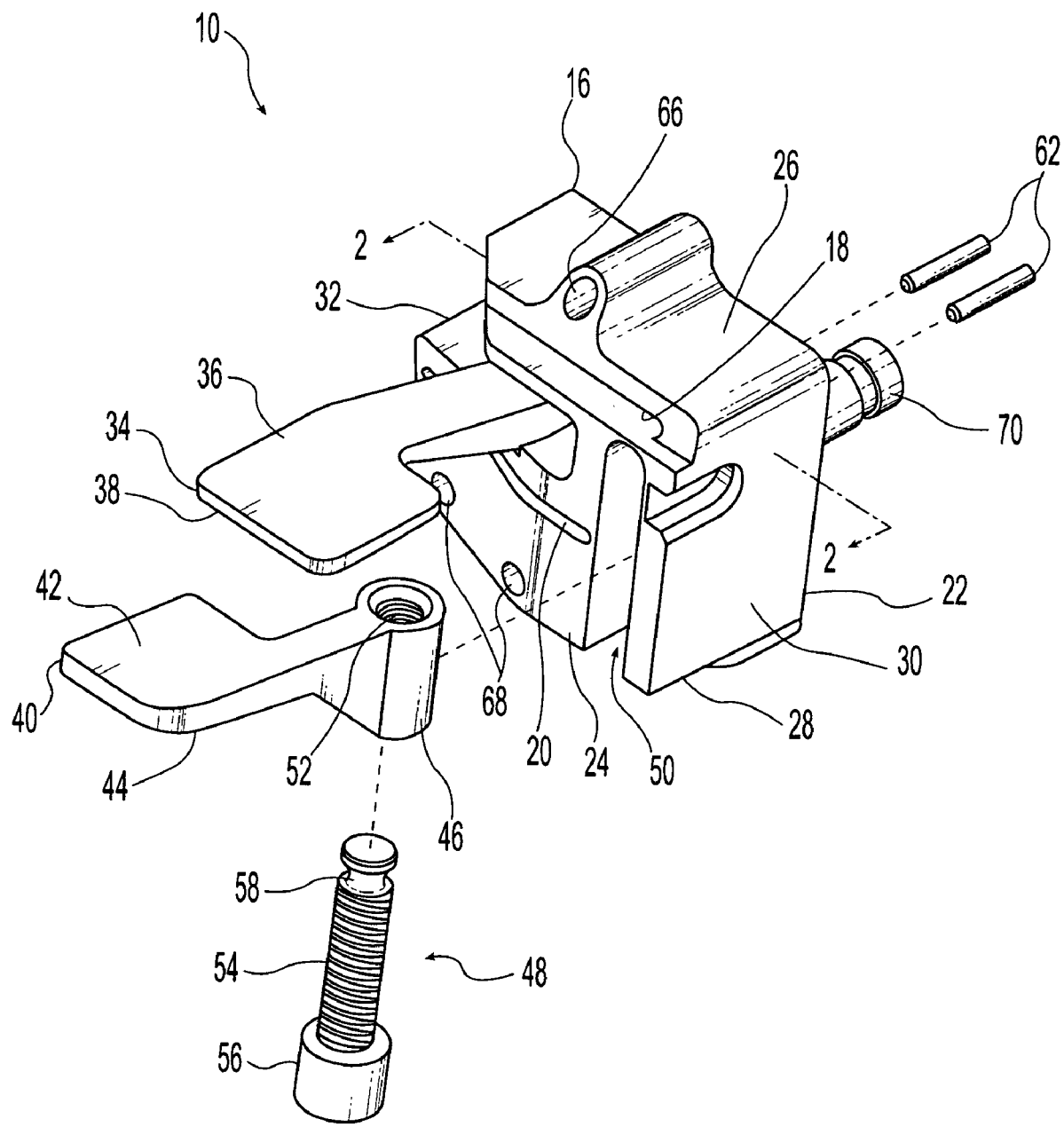
FIG. 1 is an exploded perspective view of a cut block according to the present invention.
Figure 3:
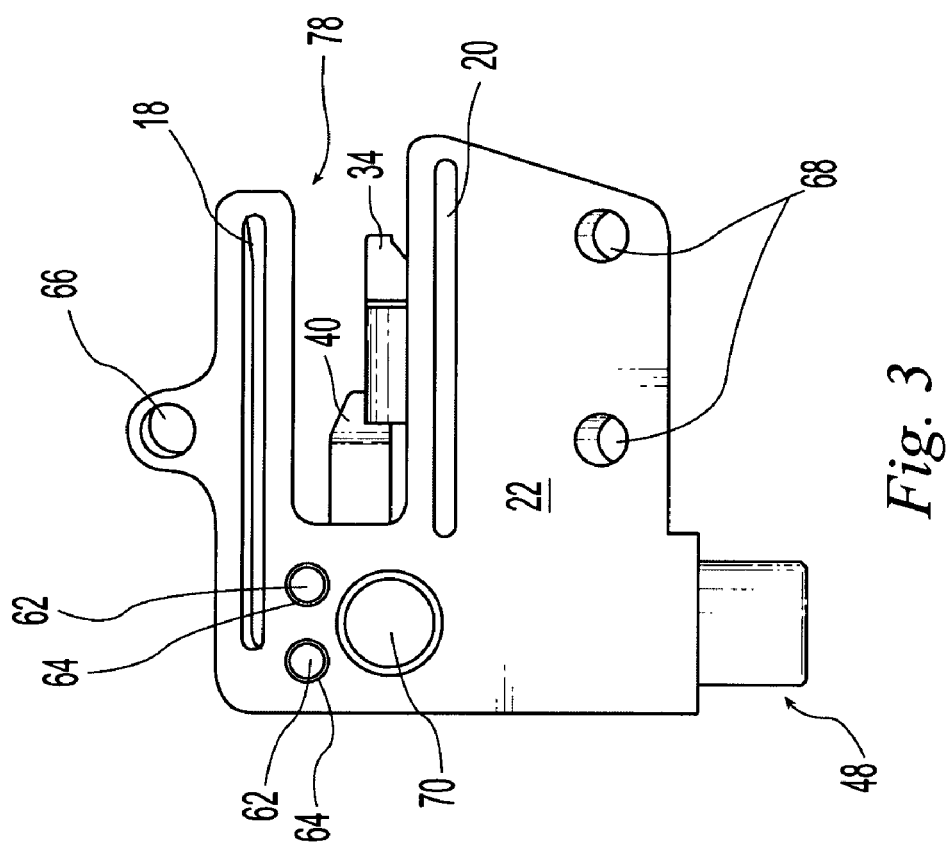
FIG. 3 is an anterior plan view of the cut block of FIG. 1.
Figure 2:
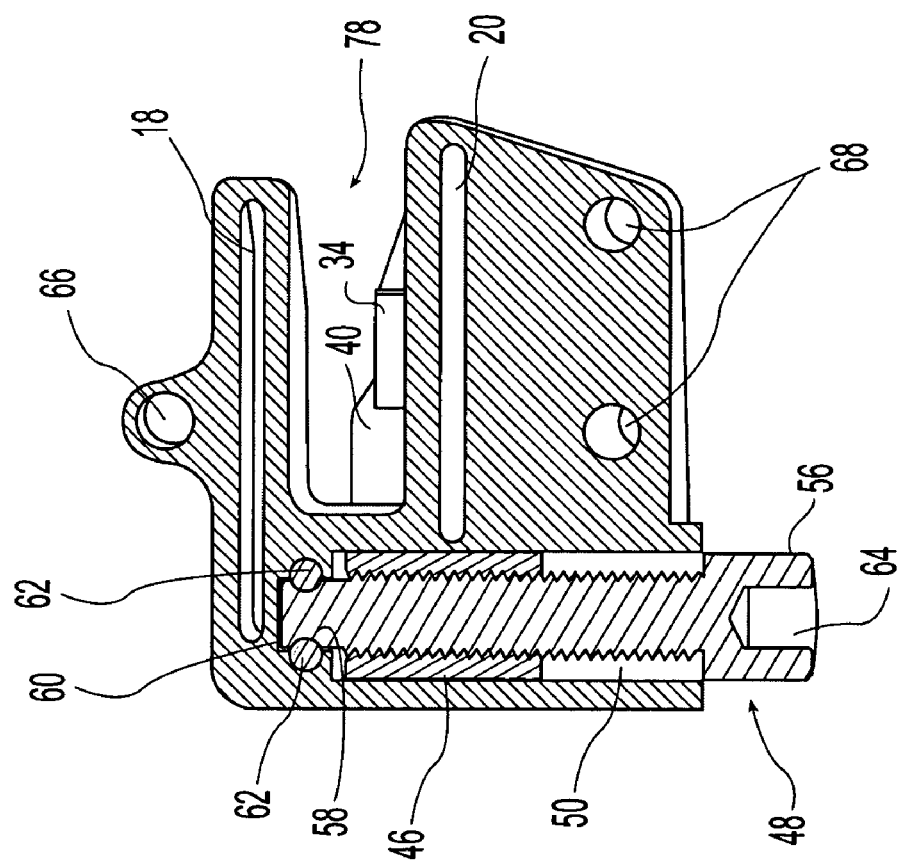
FIG. 2 is a section view taken along line 2-2 of FIG. 1.
Figure 5:
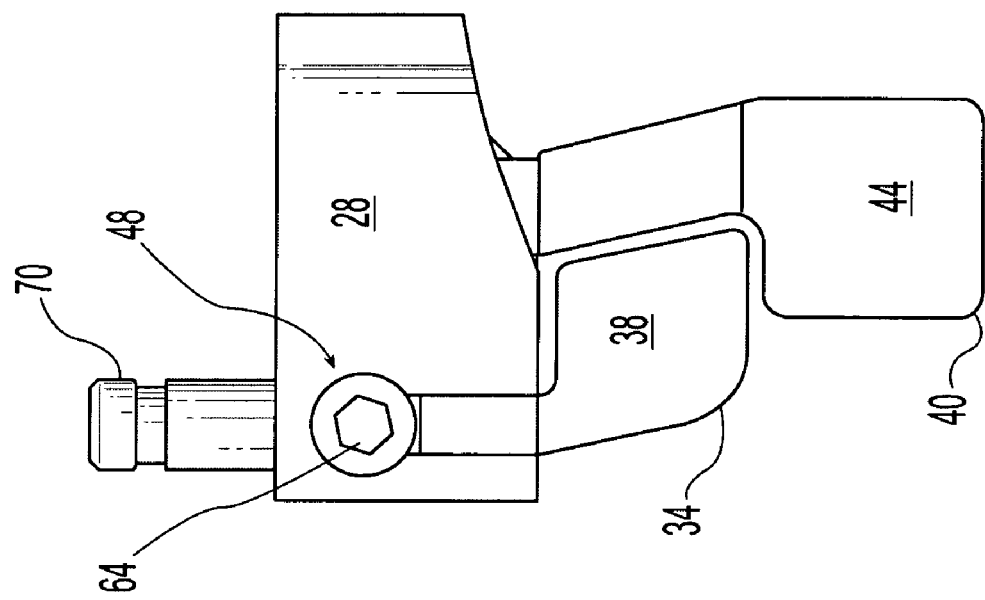
FIG. 5 is a bottom plan view of the cut block of FIG. 1.
Figure 4:
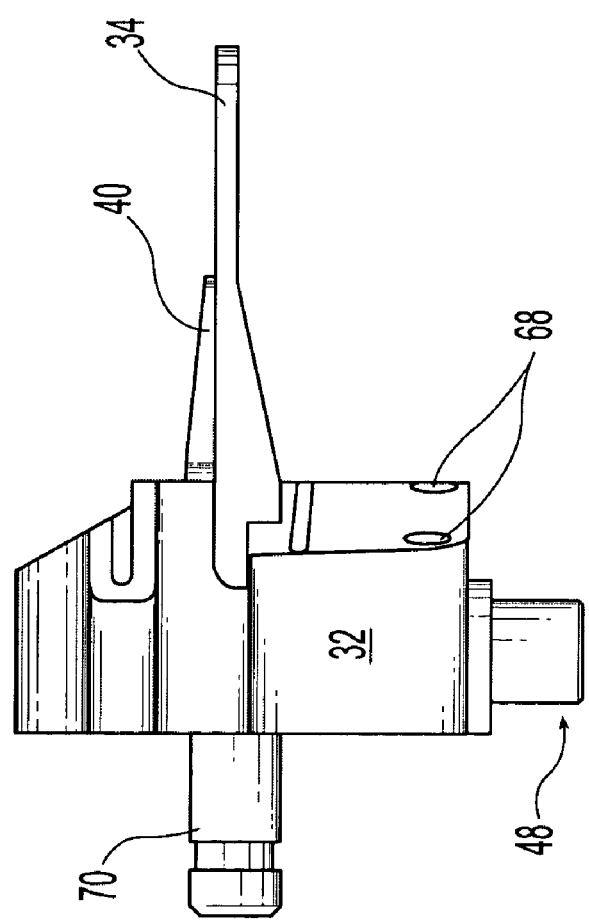
FIG. 4 is a side plan view of the cut block of FIG. 1.

FIGS. 1-7 depict an illustrative cut block 10 for cutting the femur 12 and/or tibia 14 during knee replacement surgery. The cut block 10 includes a body 16 having cutter guides for guiding a cutter to cut the femur 12 and tibia 14. In the illustrative embodiment, the cut block 10 includes a femoral cut slot 18 for guiding a saw blade to cut the femur 12 and a tibial cut slot 20 for guiding a saw blade to cut the tibia 14. By including both a femoral cut slot 18 and a tibial cut slot 20 in a single cut block, the surgeon has the choice of cutting the femur 12 first using the cut block 10 and then using a separate instrument to cut the tibia 14, cutting the tibia 14 first using the cut block 10 and then using a separate instrument to cut the femur 12, or cutting both the femur 12 and the tibia 14 with the cut block 10 in a single setup. Cutting both the femur 12 and the tibia 14 with the cut block 10 has the advantages of reducing the number of instruments, reducing the number of surgical steps, and increasing accuracy in aligning the femoral and tibial cuts relative to one another since they are produced by the same instrument without having to move the joint between cuts.

In the illustrative example (FIG. 6), the cut block 10 is depicted in use cutting the distal femur 12 and proximal tibia 14 with the knee in extension. However, the cut block 10 may also be used to cut the knee in other degrees of flexion such as 90°, 45° and other suitable angles. Also, the cut block 10 may be used to make other femoral cuts such as the posterior femoral cut, chamfer cuts, and other suitable cuts.

The cut block body 16 has an anterior face 22, a posterior face 24, a top 26, a bottom 28, and left and right sides 30, 32. The femoral and tibial cut slots 18, 20 extend through the body 16 from the anterior face 22 to the posterior face 24. In the illustrative embodiment, the femoral cut slot 18 extends perpendicular to the anterior face 22. However, the femoral cut slot 18 may be oriented at some other angle to accommodate different implant geometries and/or different flexion angles at which the cut block 10 is used. Likewise, the tibial cut slot 20 extends at a downward angle from the anterior face 22 to the posterior face 24. This angle may be approximately 7° to correspond to the anatomic posterior slope of the proximal tibia 14 or it may be any other suitable angle. The illustrative cut block 10 is configured for a left medial unicondylar knee replacement such that the left side 30 aligns generally with the medial side of the knee and the right 32 side aligns generally with the center of the knee. The cut block 10 may also be configured for use with the left lateral, right medial, and right lateral compartments in a unicondylar approach. In the illustrative embodiment, two cut blocks 10 are provided. One cut block 10 is configured for use in a left medial or right lateral procedure and another is configured for use in a right medial or left lateral procedure. The cut block 10 may also be configured for use in total knee replacement in which case it extends across both the medial and lateral compartments.

The cut block 10 further includes a first reference surface in the form of a fixed paddle 34 projecting from the posterior face 24. The fixed paddle 34 is attached to the body 16 in predetermined fixed relationship and includes a top surface 36 and a bottom surface 38. The cut block 10 further includes a second reference surface in the form of an adjustable paddle 40 mounted on the body 16 for vertical translation relative to the fixed paddle 34. The adjustable paddle 40 includes a top surface 42 and a bottom surface 44. In the illustrative embodiment, the adjustable paddle 40 is configured to move from a position in which it is generally on the same plane as the fixed paddle 34 downwardly to a position spaced below the fixed paddle 34. In this configuration, the top surface 36 of the fixed paddle 34 is at a predetermined distance below the femoral cut slot 18. Thus, placing the top surface 36 of the fixed paddle 34 against the distal femur 12 will align the femoral cut slot 18 to guide a cutter to remove a known, fixed amount of bone from the distal femur. The adjustable paddle 40 is movable downwardly such that the bottom surface 44 of the adjustable paddle 40 presses against the proximal tibia 14 to space the proximal tibia 14 away from the distal femur 12 to position the knee in a desired mechanical alignment and/or in a desired state of soft tissue balance. Thus, the adjustable paddle 40 may be adjusted so that the paddles 34, 40 hold the knee in a desired position for cutting. In the illustrative embodiment, the femoral and tibial cut slots 18, 20 are spaced vertically a known, fixed distance. By cutting the distal femur 12 and proximal tibia 14 using these two slots 18, 20, a known, fixed gap will be created between the distal femur 12 and proximal tibia 14. Inserting a knee prosthesis having a vertical height equal to the spacing between the slots 18, 20 will insure the distal femur 12 and proximal tibia 14 are positioned the same after implantation of the prosthesis as they were at the time the cuts were made.

According to the illustrative embodiment, the adjustment mechanism for the adjustable paddle 40 includes a sleeve 46 attached to the adjustable paddle 40 and an adjustment screw 48. The sleeve 46 slides up and down in a slot 50 in the body 16. The sleeve 46 further includes a vertical threaded bore 52. The adjustment screw 48 includes a threaded shaft 54 having an enlarged head 56 at one end and an annular groove 58 at the opposite end. The adjustment screw 48 threadably engages the bore 52 of the sleeve 46 and the sleeve 46 and screw 48 fit within the slot 50. The screw 48 extends vertically beyond the sleeve 46 into a circular recess 60 (FIG. 2) in the body 16 adjacent the slot 50. A pair of pins 62 is pressed into a pair of holes 64 transverse to the circular recess 60 (FIG. 2) such that the sides of the pins project into the recess 60 and are received by the annular groove 58 of the screw 48. The pins 62 restrain the screw 48 vertically while permitting the screw 48 to rotate. As the screw 48 is rotated, the sleeve 46 translates along the screw 48 such that the screw 48 may be rotated to adjust the vertical position of the adjustable paddle 40. A female hexagonal socket 64 is formed in the screw head 56 to receive a driver to facilitate rotating the screw 48.

The cut block 10 further includes one or more fixation holes 66, 68 extending from the anterior face 22 through the body 16 to the posterior face 24 to receive fixation members used to attach the cut block 10 to the bone. The fixation members may include pins, screws, and/or other suitable fixation members. In the illustrative embodiment, a single fixation hole 66 is provided adjacent the top 26 of the cut block 10 to receive a fixation member inserted into the distal femur 12 and a pair of fixation holes 68 is provided adjacent the bottom 28 of the cut block 10 to receive a pair of fixation members inserted into the proximal tibia 14.

Figure 6:
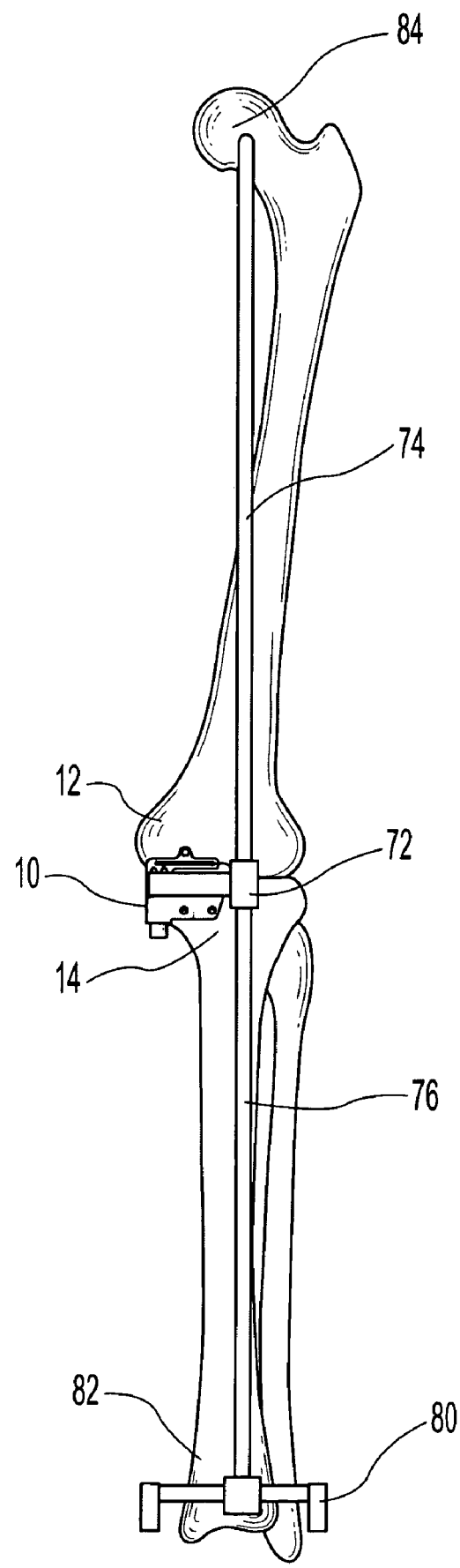
FIG. 6 is an anterior plan view of the cut block of FIG. 1 shown with alignment rods and mounted on a knee joint.
Figure 7:
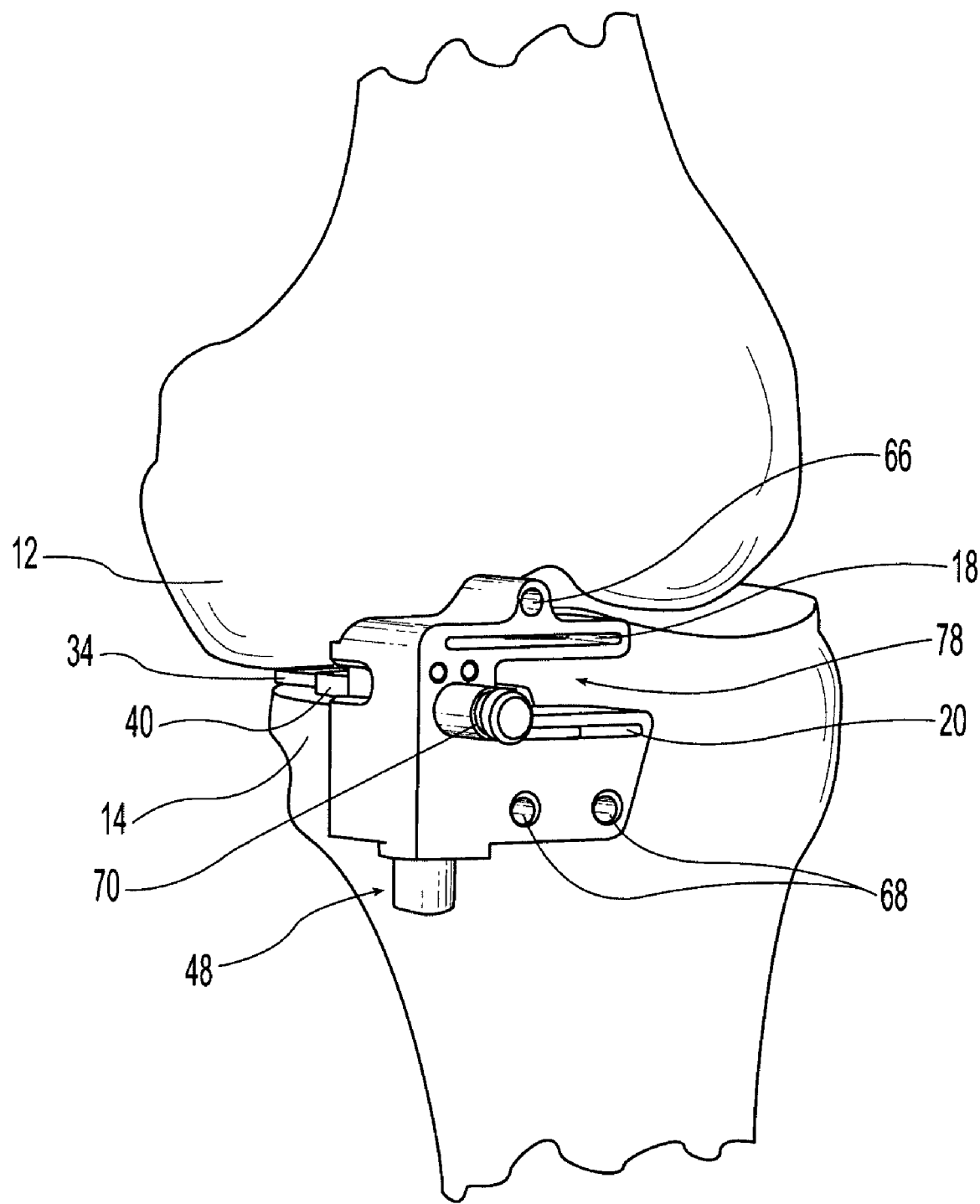
FIG. 7 is a perspective view of the cut block of FIG. 1 shown mounted on a knee joint.

The cut block 10 further includes a mounting post 70 for mounting an alignment tower 72 and alignment rods 74, 76 on the cut block 10 to aid in visualizing proper joint alignment as show in FIG. 6.

The cut block 10 further includes an opening 78 from the anterior face 22 to the posterior face 24 between the cut slots 18, 20 to permit viewing of the paddles 34, 40 through the block to verify proper paddle positioning. In the illustrative embodiment, the opening 78 also opens to the right side 32 so that the cut guide 10 body 16 forms a "C"-shape with the top of the "C" containing the femoral cut slot 18 and the bottom of the "C" containing the tibial cut slot 20.

In use, an incision is made to expose a portion of the knee joint. For example, in a medial unicondylar knee replacement, an incision is made to expose the medial compartment of the knee. An appropriate cut block 10 is selected; e.g. left medial/right lateral or right medial/left lateral. The adjustable paddle 40 is adjusted to approximately the same plane as the fixed paddle 34. The knee joint is placed in the desired position and the paddles 34, 40 are inserted between the distal femur 12 and proximal tibia 14. Optionally, upper and lower alignment rods 74, 76 may be used to further check knee position. If the alignment rods 74, 76 are to be used, an alignment tower 72 is attached to the mounting post 70. The alignment tower 72 is positioned between the femoral condyles. The lower alignment rod 76, including an ankle clamp 80, is mounted on the alignment tower 72 and extends downwardly toward the ankle 82 where it is attached to the ankle with the ankle clamp 80 as is known in the art. The upper alignment rod 74 is mounted on the alignment tower 72 and extends upwardly to point to the center of the femoral head 84. Proper knee position is indicated when the upper alignment rod 74 points to the center of the femoral head 84 and the distal alignment rod 76 is parallel to the tibial mechanical axis. Once the desired knee position is achieved, the fixed paddle 34 is positioned so that its top surface 36 abuts the distal femoral condyle and the adjustment screw 48 on the cut block 10 is turned until the adjustable paddle 40 contacts the surface of the proximal tibia 14. The paddles 34, 40 fill the space between the distal femur 12 and proximal tibia 14 to hold the joint in the desired position. The cut block 10 is then secured to the distal femur 12 and proximal tibia 14 with fixation members through the fixation holes 66, 68. If they were used, the alignment tower 72 and alignment rods 74, 76 are now removed. The distal femoral condyle is resected by guiding a saw blade through the femoral cut slot 18. The proximal tibial surface of the medial compartment is resected by guiding a saw blade through the tibial cut slot 20. Both cuts may be made without removing the cut block 10 or flexing the knee. Alternatively, headless pin fixation members may be used in the fixation holes 66, 68 to permit the cut block 10 to be lifted off of the fixation members while the knee is repositioned after the first bone cut. The cut block 10 may then be repositioned over the tibial or femoral fixation members to make the second bone cut. The fixation members are then removed and the cut block 10 is removed from the knee joint. Femoral and tibial joint replacement components are implanted to replace the portions cut away. By matching the combined component height to the distance between the cut slots 18, 20, the joint will be positioned the same after implantation of the prosthesis as it was at the time the cuts were made.

While the illustrative example has depicted a particular screw arrangement for adjusting the adjustable paddle 40, other adjustment mechanisms for changing the relative position of the paddles 34, 40 may be used and come within the scope of the invention. Other kinds of screw mechanisms, sliding mechanisms, and other suitable mechanisms may be used. Likewise, the fixed and adjustable paddles 34, 40 may be reversed. Furthermore, both paddles 34, 40 may be configured to move at the same time as their relative position is changed. For example, an arrangement (as shown) with a fixed femoral referencing paddle 34 and an adjustable tibial referencing paddle 40 is designed to always remove the same amount of bone from the femur as is appropriate where all of the femoral knee components in a system have the same thickness and the tibial component thickness is adjustable. Alternatively, an arrangement (not shown) in which the femoral referencing paddle is adjustable and the tibial referencing paddle is fixed may be used; for example, with knee components in a system with fixed tibial component thicknesses and adjustable femoral component thicknesses. Alternatively, an arrangement (not shown) in which both paddles are adjustable, either independently or simultaneously, may be uses; for example, with knee components in a system in which both component thicknesses are adjustable.

Likewise, while the illustrative examples have described reference surfaces in the form of paddles 34, 40, the reference surfaces may take other forms. For example, one or both of the reference surfaces may be in the form of a pin inserted into the bone rather than a paddle abutting the bone.

Figure 8:
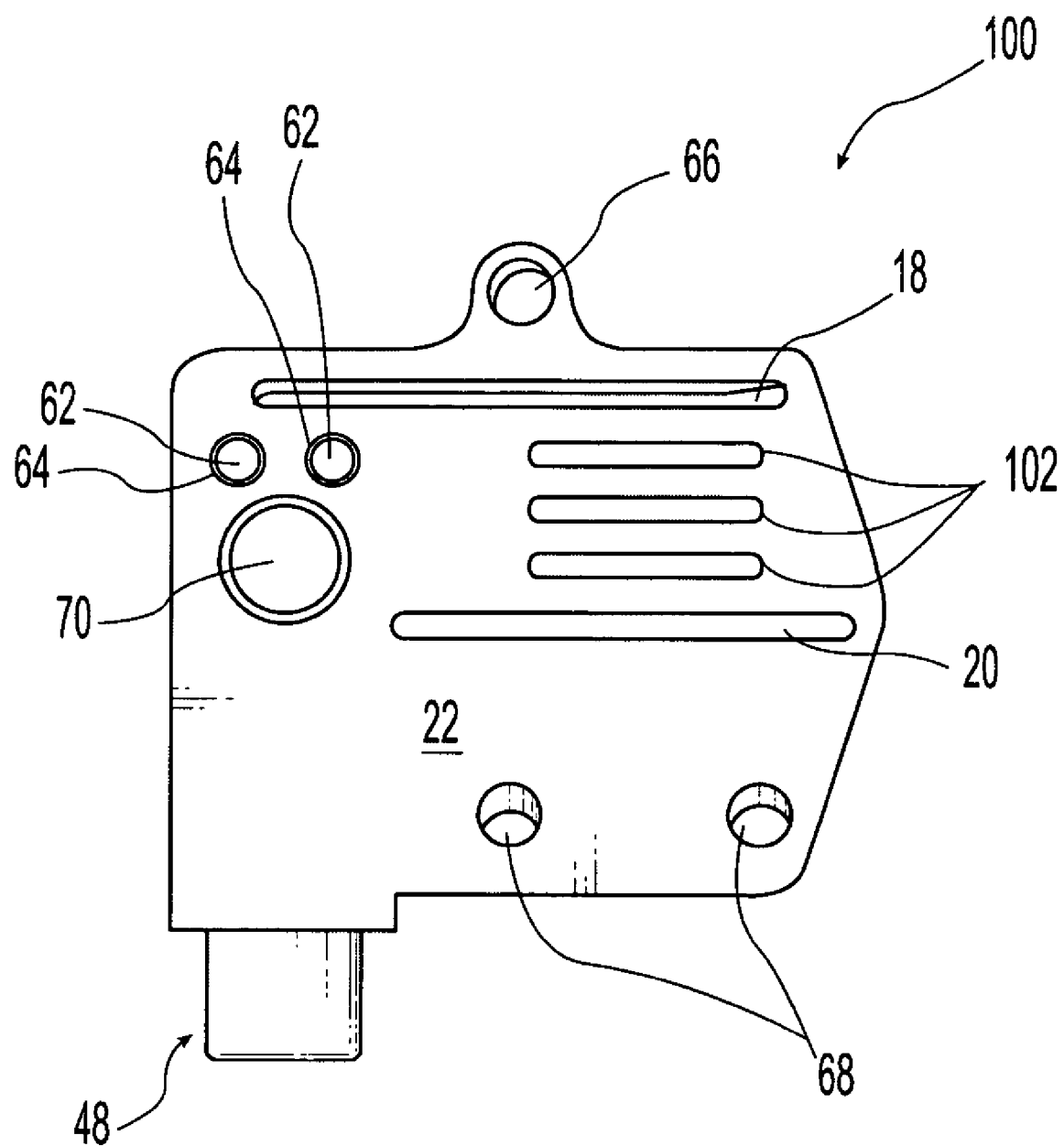
FIG. 8 is an anterior plan view of the cut block of FIG. 1 showing an alternate paddle attachment mechanism.

Likewise, the paddles 34, 40 may be permanently attached or modular. A permanently attached paddle may be formed as an integral part of the cut block 10, welded to the cut block 10, or attached in another suitable way. A modular paddle may be bolted onto the cut block, snapped into a receiving portion, carried in a slot, or otherwise be removably attached to the cut block. For example, a cut block 100 may be configured for a modular fixed paddle as shown in FIG. 8. A modular paddle may be provided to ease assembly and insertion of the cut block 100 into the surgical wound. A modular paddle may be removable after the cut depth is set to facilitate flexing of the knee joint between bone cuts. The modular paddle may permit omitting the paddle in cases where the cut depth is set in another manner such as by referencing the tibia. In the illustrative example of FIG. 8, one or more additional slots 102 may be provided at a predetermined spacing distal to the cut slot 18 and extending from the anterior face 22 to the posterior face 24. The paddle may be inserted through one of the slots 102 to project from the posterior face 24. If necessary, it may be removed by withdrawing it from the slot 102. Where multiple additional slots are provided, as shown, the femoral cut depth may be determined by appropriate slot selection.

It will be understood by those skilled in the art that the foregoing has described illustrative embodiments of the present invention and these and other variations may be made to these embodiments without departing from the spirit and scope of the invention defined by the appended claims.

What is claimed is:

1. A cut block for cutting the femur and tibia during knee joint replacement surgery, the cut block comprising:
    a body having a plurality of cutter guides for guiding a cutter to cut the femur and tibia, the body having an anterior face and a posterior face, the cutter guides comprising a femoral cut slot extending from the anterior face to the posterior face to guide a saw blade to cut the femur and a tibial cut slot extending from the anterior face to the posterior face to guide a saw blade to cut the tibia;
    a first reference surface mounted on the body and projecting posteriorly;
    a second reference surface mounted on the body and projecting posteriorly, the spacing of the first and second reference surfaces being adjustable vertically from a first position in which they are generally in the same plane to a second position in which they are spaced apart such that the reference surfaces are able to space the tibia away from the femur, the body including an opening from the anterior face to the posterior face between the cut slots to permit viewing of the reference surfaces through the block to verify proper reference surface positioning, the body further comprising a top, a bottom, a first side, and a second side extending between the anterior and posterior faces, the opening also opening toward one of the first and second sides such that the body forms a "C"-shape with the top of the "C" containing the femoral cut slot and the bottom of the "C" containing the tibial cut slot.

2. The cut block of claim 1 wherein at least one of the first and second reference surfaces comprises a pin inserted into one of the tibia and femur.

3. The cut block of claim 1 wherein at least one of the first and second reference surfaces comprises a paddle positionable in the knee joint against one of the tibia and femur.

4. The cut block of claim 1 wherein the first reference surface comprises a fixed paddle projecting from the posterior face, the fixed paddle being attached to the body in predetermined fixed relationship and the second reference surface comprises an adjustable paddle.

5. The cut block of claim 4 wherein the adjustable paddle further comprises a threaded sleeve attached to the adjustable paddle, the body further comprising a vertical slot for receiving the sleeve for vertical translation within the slot, and an adjustment screw threadably engaging the threaded sleeve, the adjustment screw being fixed to the body to permit rotation of the screw and constrain translation of the screw relative to the body such that rotation of the screw causes the sleeve and adjustable paddle to translate vertically within the slot relative to the fixed paddle.

6. The cut block of claim 4 wherein the cut block includes at least one slot extending from the anterior face to the posterior face and the fixed paddle is removably insertable in the at least one slot to attach the fixed paddle to the body in predetermined fixed relationship.

7. The cut block of claim 6 wherein the cut block includes a plurality of slots able to receive the fixed paddle such that the predetermined fixed relationship of the paddle to the body is selectable.

8. The cut block of claim 4 wherein the fixed paddle further comprises a top surface positionable adjacent the femur, and the adjustable paddle further comprises a bottom surface simultaneously positionable adjacent the tibia, the adjustable paddle being movable downwardly to a position spaced below the fixed paddle such that the bottom surface of the adjustable paddle presses against the tibia to space the tibia away from the femur.

9. The cut block of claim 1 wherein the body is sized to position the cutter guides over one side of the knee for a unicondylar knee replacement procedure, one of the first and second sides being positionable adjacent an outer portion of the knee and the other of the first and second sides being simultaneously positionable adjacent the center of the knee.

10. The cut block of claim 1 wherein the body sized to position the cutter guides over the knee for a total knee replacement procedure, one of the first and second sides being positionable adjacent the medial side of the knee and the other of the first and second sides being simultaneously positionable adjacent the lateral side of the knee.

* * * * *